(12) United States Patent
Grasmeder et al.

(10) Patent No.: US 10,179,318 B1
(45) Date of Patent: Jan. 15, 2019

(54) METHOD FOR GENERATING FORMALDEHYDE MONOMER VAPOR

(71) Applicant: Airgas, Inc., Radnor, PA (US)

(72) Inventors: Robert J. Grasmeder, Perkasie, PA (US); Stephen B. Miller, Doylestown, PA (US); Nolan R. Petrich, Doylestown, PA (US)

(73) Assignee: Airgas, Inc., Radnor, PA (US)

( * ) Notice: Subject to any disclaimer, the term of this patent is extended or adjusted under 35 U.S.C. 154(b) by 0 days.

(21) Appl. No.: 15/710,139

(22) Filed: Sep. 20, 2017

(51) Int. Cl.
| | |
|---|---|
| *C07C 47/04* | (2006.01) |
| *B01J 7/00* | (2006.01) |
| *B01J 19/00* | (2006.01) |
| *B01J 8/00* | (2006.01) |
| *B01J 8/02* | (2006.01) |
| *F28D 7/04* | (2006.01) |
| *C08G 65/16* | (2006.01) |
| *B01J 19/18* | (2006.01) |
| *C07C 25/02* | (2006.01) |

(52) U.S. Cl.
CPC ............. *B01J 8/0292* (2013.01); *C07C 47/04* (2013.01); *C08G 65/16* (2013.01); *F28D 7/04* (2013.01); *B01J 19/1812* (2013.01); *C07C 25/02* (2013.01); *C08G 2650/44* (2013.01)

(58) Field of Classification Search
CPC ......... C07C 47/04; B01J 7/00; B01J 19/2415; B01J 19/1812
See application file for complete search history.

(56) References Cited

U.S. PATENT DOCUMENTS

| | | | | |
|---|---|---|---|---|
| 2,460,592 A | * | 2/1949 | Miller, Jr. ................ | B01D 7/00 568/457 |
| 2008/0191153 A1 | * | 8/2008 | Marganski ................ | B01J 7/00 250/492.21 |

* cited by examiner

*Primary Examiner* — Sikarl A Witherspoon
(74) *Attorney, Agent, or Firm* — Elwood L. Haynes (57) ABSTRACT

A method of generating a desired gas is provided. The method includes introducing a matrix comprising media containing a parent compound and an inert media into an effusion tube comprising a first zone and a second zone. The first zone includes a micro-porous metal tube, and a closed end. The second zone includes a non-porous metal tube, and an open end. Heating the effusion tube, produces a desired gas.

16 Claims, 8 Drawing Sheets

METHOD FOR GENERATING FORMALDEHYDE MONOMER VAPOR

BACKGROUND

Formaldehyde is a toxic chemical substance that is commonly present in indoor and outdoor air pollution. Indoors, materials like furniture, carpets and household chemicals emit formaldehyde; outdoors, formaldehyde is generated through incomplete combustion of coal and fuels, and is commonly found in automotive emissions and stationary sources (stacks) that burn carbon-based fuels. There is considerable interest in having the ability to make accurate measurements of formaldehyde to assess the fate and health consequences of formaldehyde emissions, as well as to promulgate new regulations to control these emissions.

The current manufacturing process for calibration standards for formaldehyde makes use of an analytical-scale permeation device. This device generates formaldehyde vapor by heating alpha-polyoxymethylene (a solid polymer of formaldehyde) in a sealed vessel and allowing the small amount of generated formaldehyde monomer vapor to diffuse through a length of Teflon® PTFE tubing into a flowing gas stream. Although it does successfully produce formaldehyde gas for mixtures, the extremely low rate of formaldehyde emission makes this process very lengthy and impractical for large quantities of cylinders.

Although it is a small molecule with a low molecular weight, formaldehyde does not persist as a gas phase at high concentration in the pure form. Formaldehyde undergoes self-reaction to form polymers of itself (such as paraformaldehyde) and a variety of larger organic molecules by condensation reactions. Formaldehyde can be stabilized as a monomer in solutions with organic solvents or water (formalin).

However, aqueous solutions are not suitable for component additions to gas cylinders, as moisture almost always adversely affects mixture stability. Therefore, pure, dry and uncontaminated formaldehyde must be generated in-situ as needed from materials that emit formaldehyde when heated, such as paraformaldehyde, trioxane and even gum rubber tubing.

Describe herein is a new technique and a new apparatus for controlled generation of formaldehyde monomer vapor. This new process generates larger quantities and higher concentrations of formaldehyde, thereby facilitating faster production of mixtures in gas cylinders. This new process also minimizes decomposition of formaldehyde via self-reaction as well as formation of undesired side products.

SUMMARY

A method of generating a desired gas is provided. The method includes introducing a matrix comprising media containing a parent compound and an inert media into an effusion tube comprising a first zone and a second zone. The first zone includes a micro-porous metal tube, and a closed end. The second zone includes a non-porous metal tube, and an open end. Heating the effusion tube, produces a desired gas.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF PREFERRED EMBODIMENTS

Element Numbers
- 100=closed-end microporous metal tube
- 101=first zone (microporous section of closed-end microporous metal tube)
- 102=second zone (solid section of closed-end microporous metal tube)
- 103=closed end (of closed-end microporous metal tube)
- 104=open end (of closed-end microporous metal tube)
- 105=formaldehyde-generating precursor
- 106=inert media
- 107=matrix (of formaldehyde-generating precursor and inert media)
- 200=outer metal jacket
- 201=steel cap (to close open end)
- 202=run tee (union tee)
- 203=tubing reducer
- 204a=compression tube fitting (integral to run tee 202)
- 204b=reducing union
- 204c=compression tube fitting (integral to run tee 202)
- 205=carrier gas
- 205a=unheated carrier gas
- 205b=heated carrier gas
- 205c=warm carrier gas
- 206=gas entry port (of outer metal jacket)
- 207=gas exit port (of outer metal jacket)
- 208=annular region (between closed-end microporous metal tube and outer metal jacket)
- 701=heating device
- 702=pure formaldehyde monomer vapor
- 703=desired formaldehyde mixture
- 704=variable input heating control (generator temperature controller)
- 705=temperature indicator
- 706=temperature indicator
- 707=flow indicator
- 708=flow indicator
- 709=composition indicator
- 710=gas composition controller
- 711=valve
- 712=external heat source
- 713=temperature indicator 714=carrier gas flow controller
715=gas cylinder As illustrated in FIGS. 1-8, the general design of the apparatus comprises a closed-end, micro-porous metal tube 100 captured inside of an outer metal jacket 200. The micro-porous metal tube 100 has a first zone 101 that consists of a micro-porous wall, and a second zone 102 that consists of a non-porous wall. The porosity of the first zone 101 may be 0.1 to 5.0 microns, such tubes are commercially available. The first zone 101 has a closed end 103. The second zone 102 has an open end 104. In the following example, formaldehyde gas is used as a non-limiting example. However, as discussed below, the instant apparatus may also be used to generate other desired gases.

Figure 1:
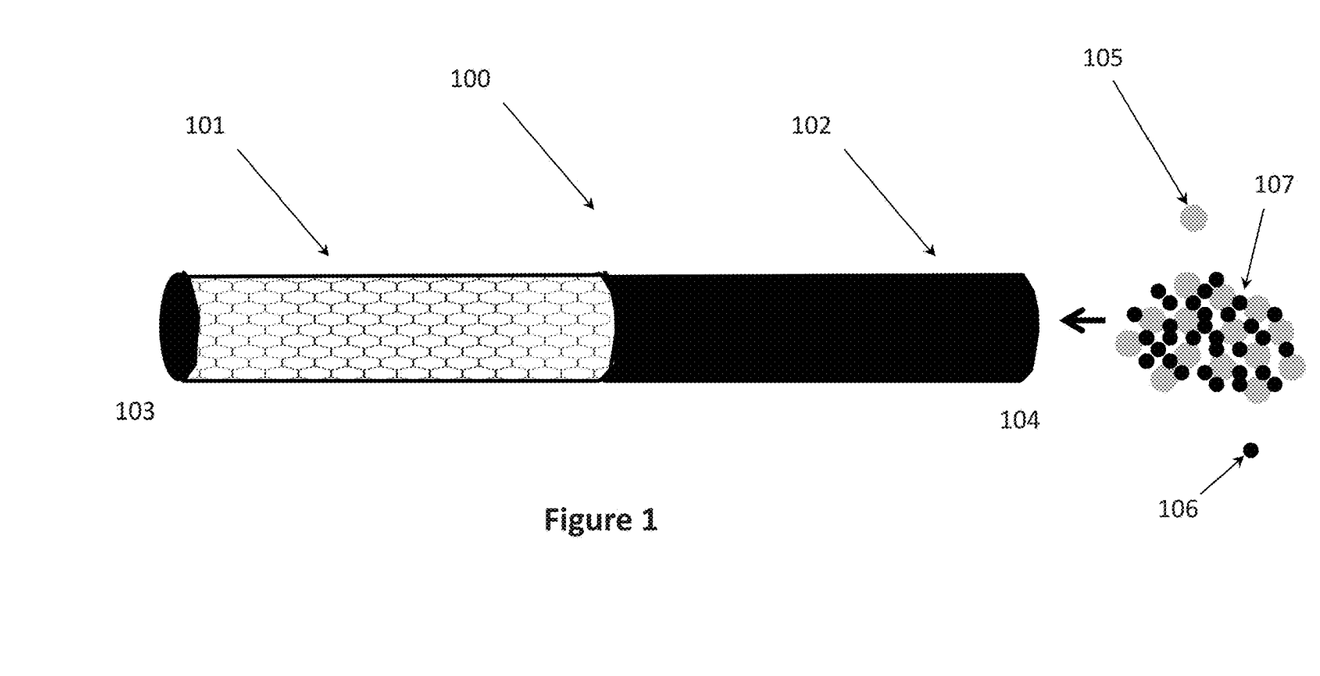
FIG. 1 is a schematic representation of the closed-end microporous metal tube, illustrating the microporous section, the solid section, and the introduction of the matrix.
Figure 3:
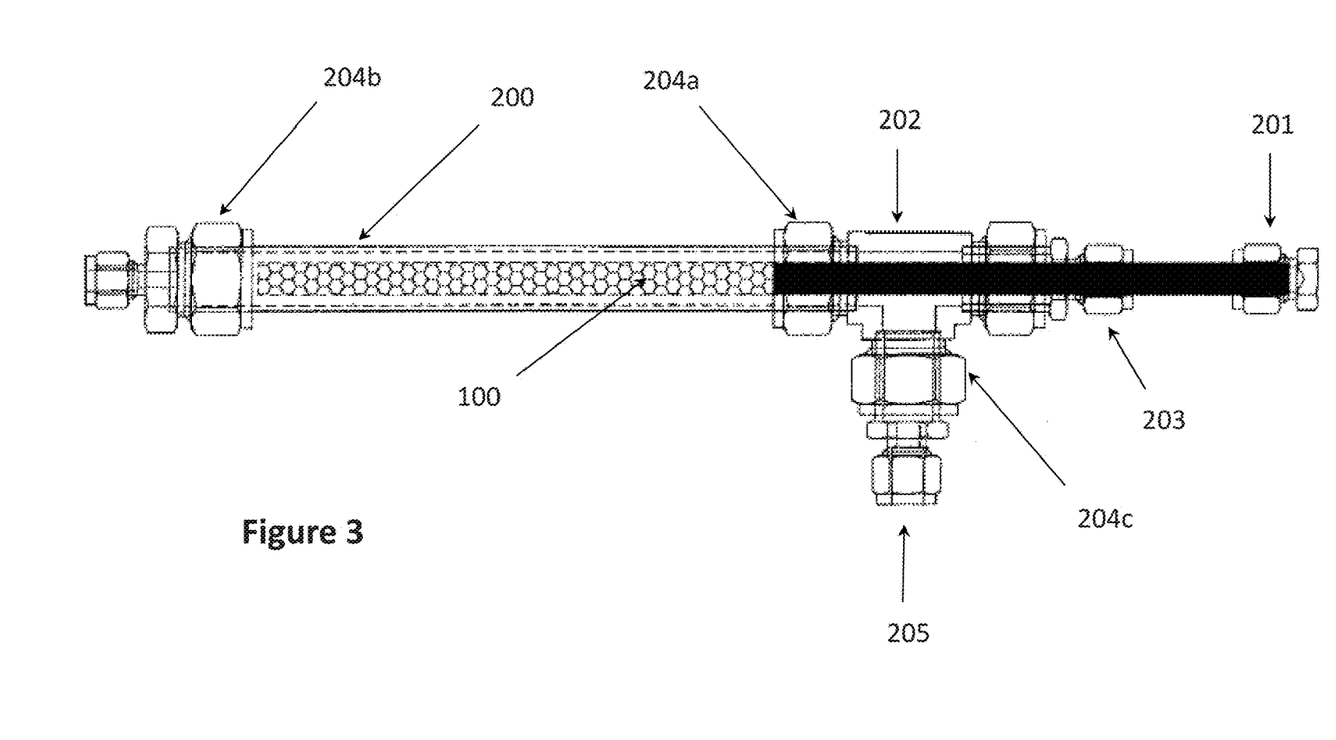
FIG. 3 is a schematic representation of the outer metal jacket, illustrating its placement within the run tee.

A formaldehyde-generating precursor 105 is packed inside of the porous metal tube 100. The formaldehyde-generating precursor 105 may be combined with an inert media 106 to form a matrix 107. Matrix 107 is then introduced into the metal tube 100, and the open end is capped gas tight, for example with steel cap 201. The filled porous tube 100, also referred to herein as the permeator, is then passed through the full length of a union tee, or run tee, 202. The run tee 202 is attached to the outer metal jacket 200 and secured with at least one high pressure compression fitting, for example, a tubing reducer 203.

The outer metal jacket 200 is equipped with compression tube fittings, such as 204a which is integral to run tee 202, capable of high pressure (typically about 2000 psig). Another high pressure compression tube fitting is at the exit end of outer metal jacket 200, such as reducing union 204b, and the other on the leg portion 204c, also integral to run tee 202, through which carrier gas 205 flows.

In one representative, but non-limiting, example, the closed-end microporous metal tube 100 may be nominally ⅜ inches in diameter, and outer metal jacket 200 may be nominally ¾ inches in diameter. Fittings such as run tee 202, reducing union 204b, and steel cap 201 in sizes such as these are commercially available.

Figure 7:
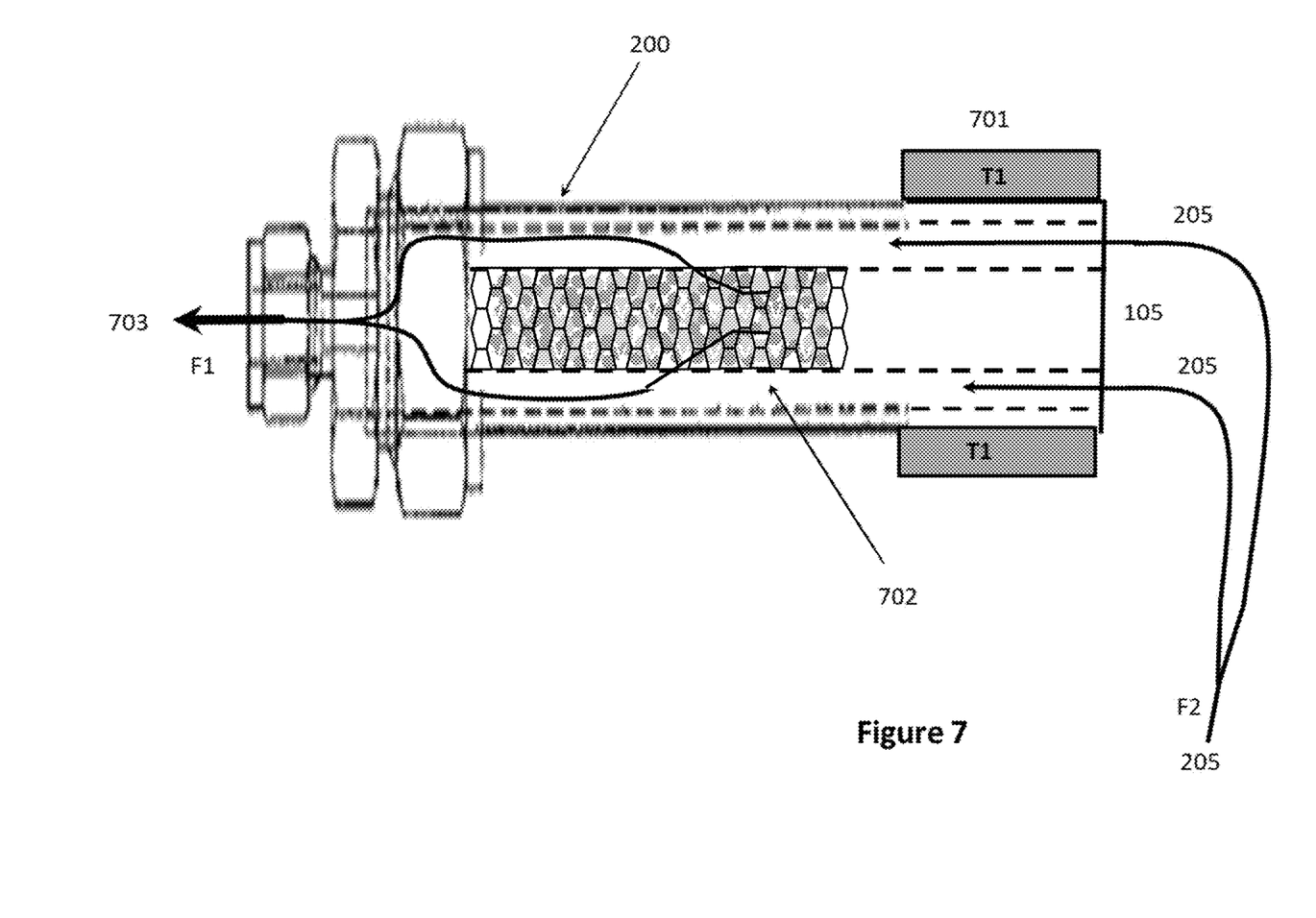
FIG. 7 is a schematic representation of the invention illustrating the flow of carrier gas and the flow of pure formaldehyde monomer vapor.

The exterior of outer metal jacket 200 is then heated by heating device 701 to a controlled temperature, for example by variable input heating control 704, sufficient to de-polymerize the formaldehyde-generating precursor 105 and liberate pure formaldehyde monomer vapor 702. The formaldehyde vapor 702 escapes by passing through the interstices of the porous microporous metal tube 101 as a gas. While formaldehyde monomer vapor 702 is being formed, carrier gas 205 is passed through annular region 208 between the metal tube 100 and outer metal jacket 200 at a controlled rate to entrain the liberated vapor 702. The carrier gas 205 is the same composition as the balance gas of the desired formaldehyde mixture 703, typically nitrogen, helium or argon.

Figure 8:
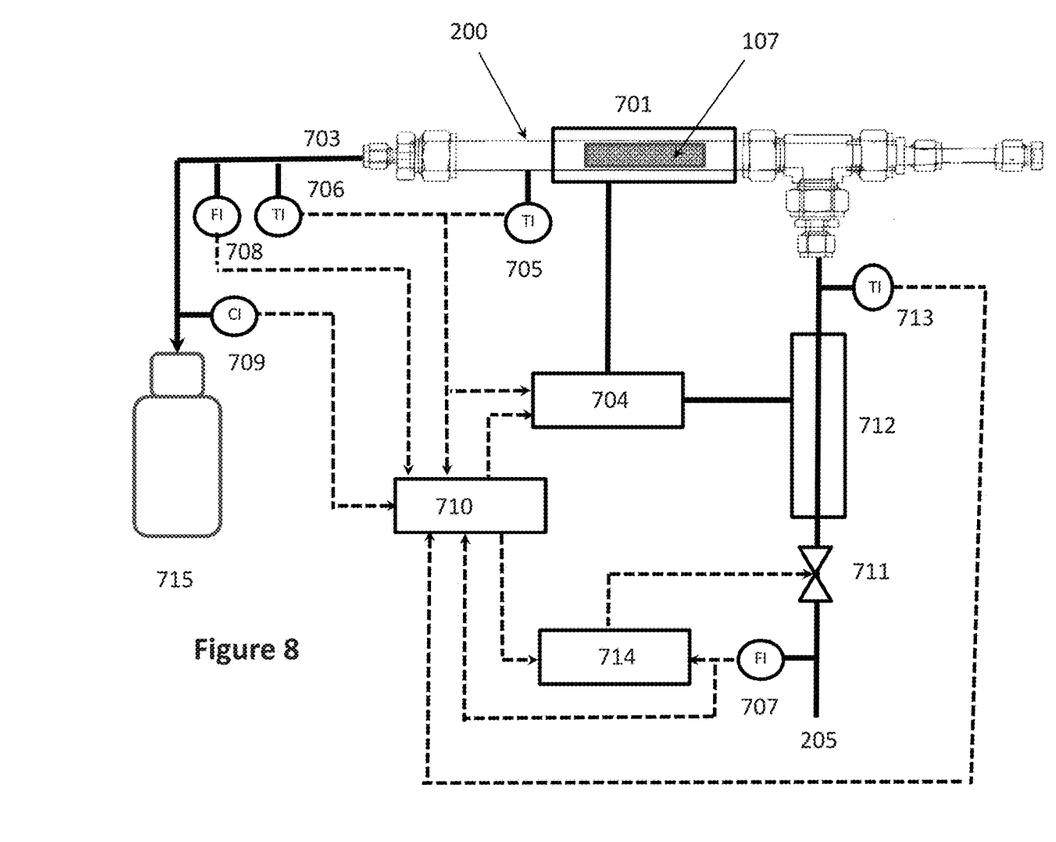
FIG. 8 is a schematic representation of the invention illustrating the overall process scheme.

Close control of the temperature of the outer metal jacket 200 results in a predictable emission rate of formaldehyde vapor 702. Higher temperatures increase the emission rate, but excessive heating results in undesirable side reactions and contamination. The composition controller 710 does not control the outer metal jacket temperature; the controllers for the heating devices do. The temperature may be monitored directly on the outer metal jacket 200, for example, by temperature indicator 705, or the temperature of the gas exiting the permeator may be monitored, for example, by temperature indicator 706. The flow rate of carrier gas 205 may be monitored, for example, by flow indicator 707, and/or the total flowrate of the formaldehyde mixture 703 may be monitored, for example, by flow indicator 708. The final composition of the formaldehyde mixture 703 may be monitored, for example, by composition indicator 709. Close control of the carrier gas flow rate 205, in conjunction with close control of the permeator heating 704, for example, by gas composition controller 710, results in a flowing stream of formaldehyde gas (or vapor) 702 in the selected carrier gas 205 with a predictable, stable and controllable concentration.

In another embodiment of the current invention, the carrier gas 205 itself is externally heated prior to entry to outer metal jacket 200, for example by external heat source 712. In this embodiment, the heat of carrier gas 205 is used to cause the de-polymerization of the formaldehyde precursor 107 inside the permeator tube 100. The temperature may be monitored, for example, by temperature indicator 713, and provided as input to gas composition controller 710, or carrier gas flow controller 714.

Figure 5:
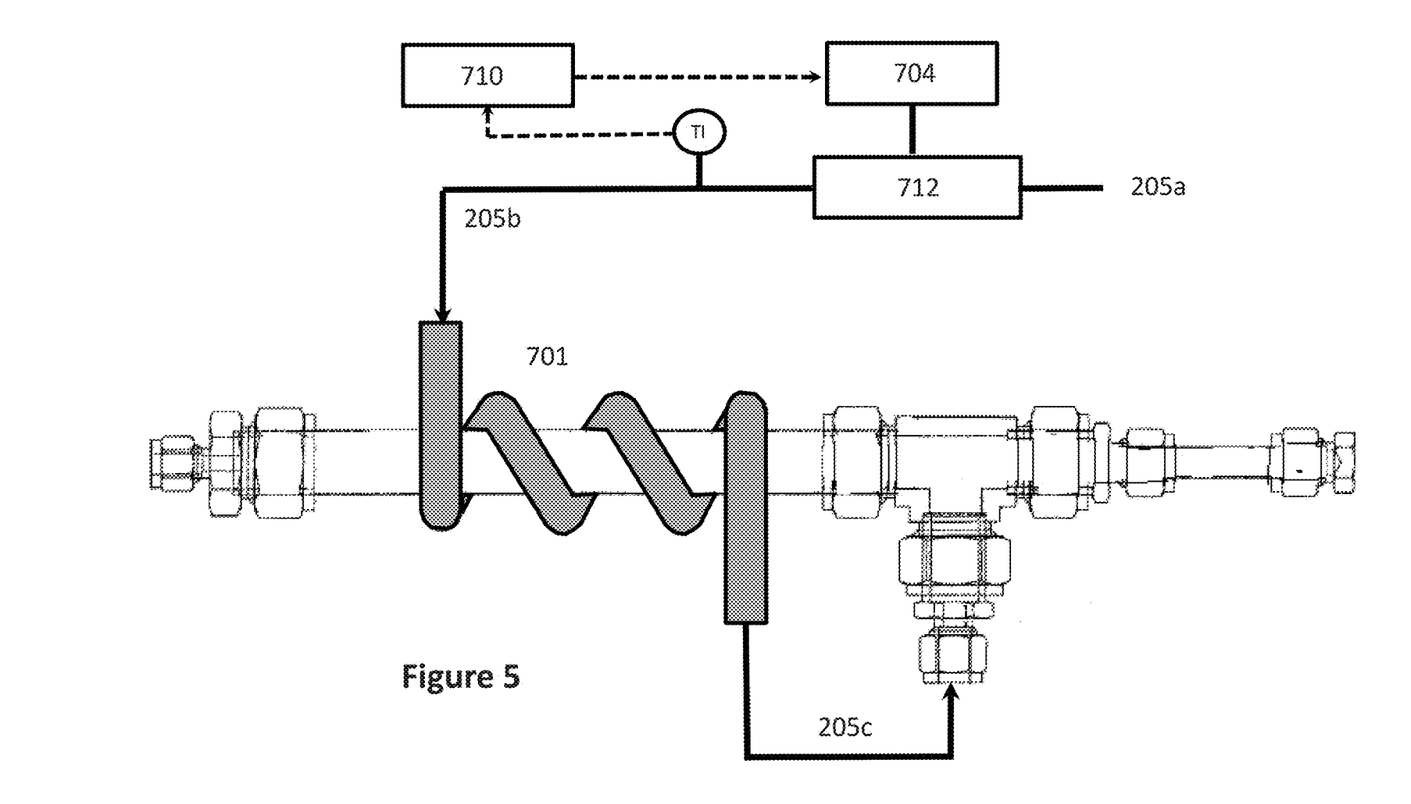
FIG. 5 is a schematic representation of the invention illustrating the heating device, in this case heated metal tubing.

In another embodiment of the current invention, as indicated in FIG. 5, the outer metal jacket 200 is wrapped with a tight coil of small diameter metal tubing 701. In a non-limiting example, this metal tubing may have a nominal outside diameter of ⅛". Carrier gas 205a is passed through an external heater 712 as discussed above. The heated carrier gas 205b is then passed through the coil 401. The heated carrier gas 205b heats the outer metal jacket 200 externally. Then the resulting warm carrier gas 205c, enters run tee 202 as discussed above, and then heats the permeator internally, potentially resulting in improved temperature control.

It is known in the art that various materials emit formaldehyde when heated. Non-limiting examples include paraformaldehyde, trioxane and even gum rubber tubing. Commercially available analytical permeation systems typically use formaldehyde polymers as the source because of their convenient handling properties, such as being colorless granular solids. However, the skilled artisan would be aware of charring and melting of the paraformaldehyde when it is over-heated, thus resulting in reduced yield and purity.

In one early reference, U.S. Pat. No. 2,460,592, it is suggested to suspend finely ground paraformaldehyde powder in a stirred liquid medium, such as a non-reactive oil and fluid with a low vapor pressure. In this reference, very pure formaldehyde vapor is then generated when the liquid media is heated. This approach, however, will not work in a cylinder gas application, as such an application has stringent dryness standards, and cannot tolerate liquid media of any kind.

In one embodiment of the present invention, finely-divided paraformaldehyde powder (or other formaldehyde-emitting material) 105 is suspended in a non-reactive solid dispersing medium 106, such as pure silica, alumina or other inorganic substrate. The dispersing media 106 is very pure, dry and completely free of organic materials that can react with formaldehyde; both silica and alumina are commercially available in adequate purities. The particle size distribution of the support media 106 is sufficiently small that it disperses the paraformaldehyde powder particles 105 from one another (to suppress self-reaction when heated), but sufficiently large to retain all of the support media 106 and paraformaldehyde particles 105 inside of the permeator porous housing 100. The support media 106 also provides uniform heat distribution within the mixture 107 and may accelerate the rate at which formaldehyde vapor 702 is formed due to increased surface area. As the formaldehyde vapor 702 is formed, the dispersing media 106 stays behind in the permeator 100, along with any other solids or non-volatile contaminants.

The present invention, i.e., dispersing materials onto a solid support and then forming a controlled gas stream using the porous metal permeator, may also be applicable to other materials that require moderate heating to force them into the gas phase, e.g., materials that emit a desired component when heated, or that have low native vapor pressure at room temperature.

Figure 4:
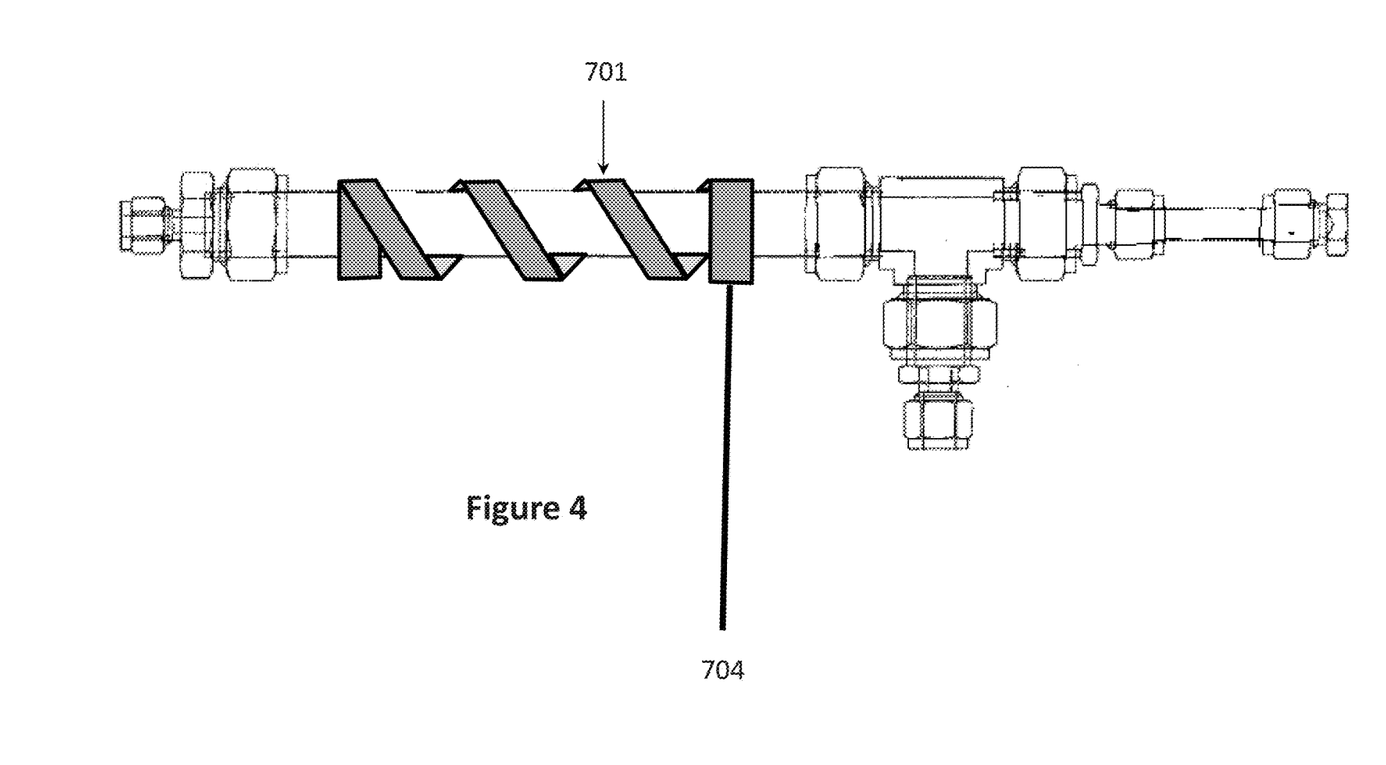
FIG. 4 is a schematic representation of the invention illustrating the heating device, in this case heat tracing.

The heating device 701, whether directly attached to the outer metal jacket 200, or integrated into the carrier gas flow system 205 (as discussed above), is equipped with variable input control capable 704 of making fine adjustments to the temperature. The outer metal jacket 200 of the formaldehyde generator is fitted with one or more temperature indicators, or thermocouples, 705 to measure the temperature, and provide feedback to the heating device to achieve closed loop control 710 of the temperature.

The generator system can also be equipped with real-time analysis 710 of the concentration 708 of the formaldehyde/carrier gas stream 703 as it is formed. To achieve this, a tee is installed in the carrier gas output line, downstream of the generator. A small bypass flow from the formaldehyde/carrier gas mixture stream is directed to a formaldehyde analyzer 708. Analyzer 708 may be a chemical cell, FTIR or other formaldehyde sensor known in the art. Any changes in the formaldehyde emission rate or carrier gas flow can thus be measured directly, and adjustments made to temperature or carrier gas flow rate, for example by valve 711. If desired or practical, the output from the real-time analyzer 710 can be fed back to the generator temperature controller 704, or the carrier gas flow controller 714, or both to achieve closed loop control.

In one embodiment of the present invention, a method of generating a desired gas is presented. The method includes matrix 107 which includes media containing parent compound 105, i.e., a precursor to the desired gas, and inert media 106. Matrix 107 is introduced into effusion tube 100 which includes first zone 101 and second zone 102. The first zone 101 includes a micro-porous metal tube, and closed end 103. The second zone 102 includes a non-porous metal tube, and open end 104. Effusion tube 100 is heated, thus producing the desired gas 702.

Figure 2:
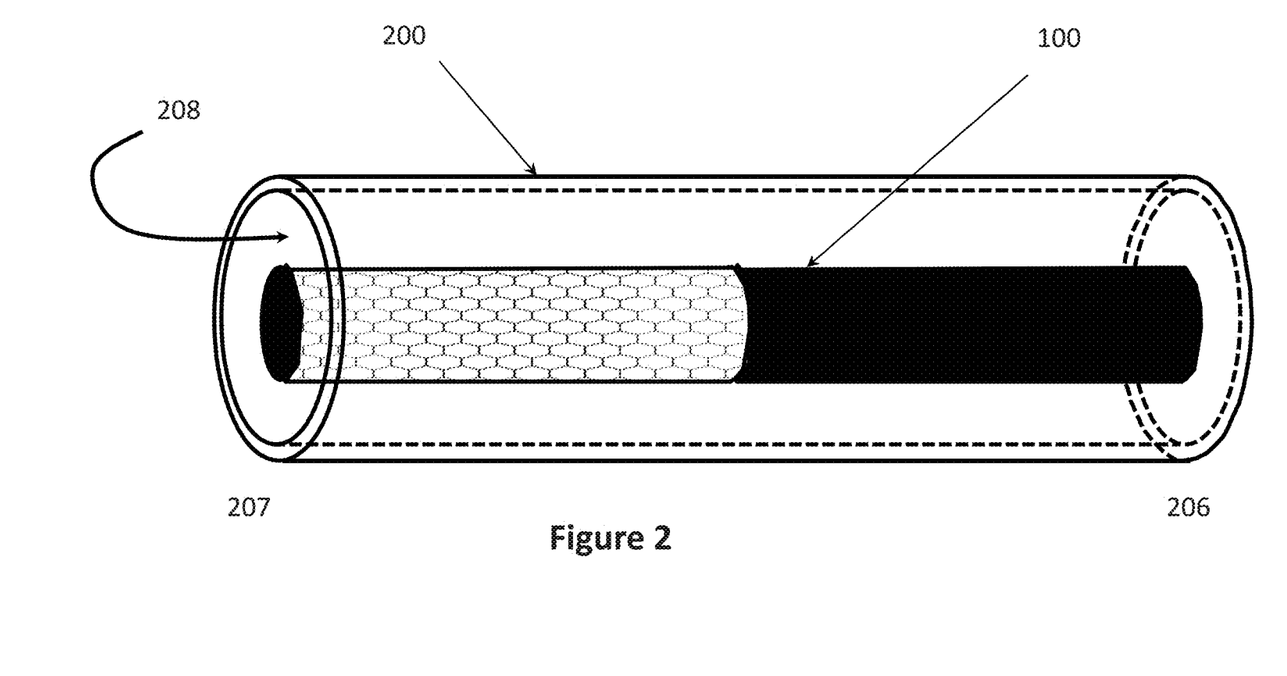
FIG. 2 is a schematic representation of the closed-end microporous metal tube illustrating its placement within the outer metal jacket, and the resulting annular region.

The two-zone effusion tube 100 may be fixtured inside of a larger cylindrical metal jacket 200. The cylindrical metal jacket 200 may have gas entry port 206 and gas exit port 207 at opposite ends. Annular region 208 is formed between inner effusion tube 100 and outer cylindrical metal jacket 200. Carrier gas 205 flows through this annular region 208 and over the exterior of effusion tube 100.

Desired gas 702 may be formaldehyde, and parent compound 105 may be paraformaldehyde, alpha-polyoxymethylene (no space between poly and oxy), trioxane or other material that emits formaldehyde when heated. Desired gas 702 may be 1,4-dichlorobenzene; 1,3,5-trichlorobenzene; 1,2,4,5-tetrachlorobenzene; 1,2,4,5-tetramethylbenzene; camphor; hexachlorobenzene; hexamethylcyclotrisiloxane; indole; menthol; naphthalene; p-cresol; phenol; or any other low vapor pressure chemical. Parent compound 105 may be the solid, semi-solid or liquid form of the desired gas 702.

Figure 6:
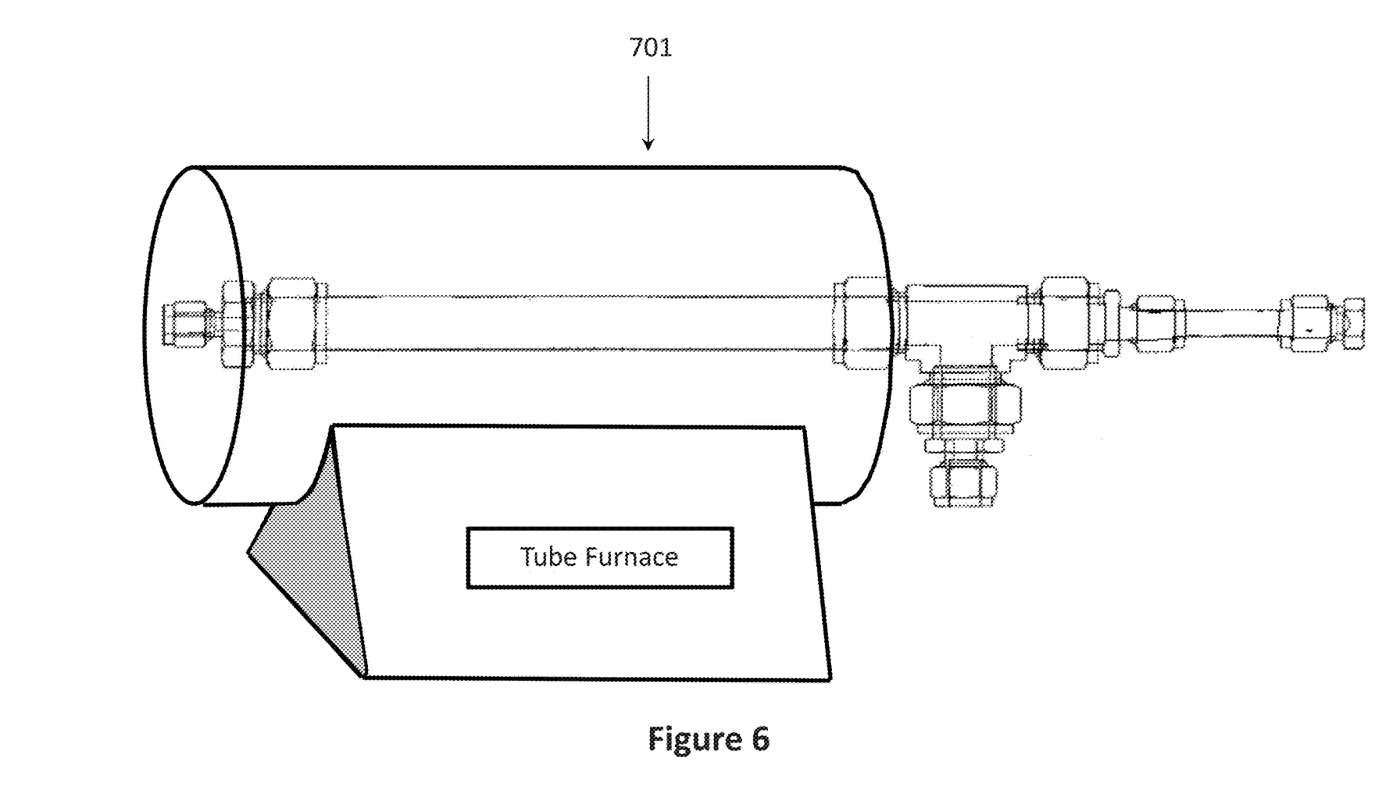
FIG. 6 is a schematic representation of the invention illustrating the heating device, in this case a tube furnace.

Effusion tube 100 may be heated to a temperature no greater than 482 F. At least a portion of the heat to effusion tube 100 may be provided heating device 701, which may be heating tape, rope heater, heating cable, or heating cord in contact with metal jacket 200. At least a portion of the heat to the effusion tube may be provided by a tube furnace 701 that heats the outside of metal jacket 200.

Desired gas 702 may be generated at a rate up to 50 grams per hour. The carrier gas 205 may be introduced into the annular region 208, wherein the carrier gas 205 blends with desired gas 702 and exits the open end 207 of metal jacket 200.

Blended gas 702 may have a first flow rate F1, (which will be approximately the same as the carrier gas second flow rate F2). The effusion tube may have a first temperature T1, and first flow rate F1 may be controlled by adjusting the carrier gas flow rate F2. T1 is not an adjustment for flow; it has very little effect on flow. Carrier gas 205 may provide at least a portion of the heat to effusion tube 100. Carrier gas 205 may be nitrogen, helium, argon, air, or other gas that is non-reactive with the desired gas 702. Blended gas 703 may be produced at a pressure up to about 2500 psig. Blended gas 703 may be produced at a pressure up to about 500 psi, preferably up to about 1000 psi, more preferably up to about 1200 psi, still more preferably up to about 1650 psi, and more preferably up to about 2200 psi.

The desired gas 703, or the blended gas, may be introduced into gas cylinder 715. Once the desired gas 703 is vaporized, the inert matrix 106 may retain some or all of the residue of the parent compound 105.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method of generating a desired gas, comprising:
   introducing a matrix comprising media containing a parent compound and an inert media into an effusion tube comprising a first zone and a second zone,
   wherein the first zone comprises a micro-porous metal tube, and a closed end,
   wherein the second zone comprises a non-porous metal tube, and an open end, and
   heating the effusion tube, thereby producing a desired gas.

2. The method of claim 1, wherein the two-zone effusion tube is fixtured inside of a larger cylindrical metal jacket with gas entry and exit ports at opposite ends of the jacket, which allows gas to flow over the exterior of the effusion tube.

3. The method of claim 1, wherein the desired gas is formaldehyde, and the parent compound is paraformaldehyde, alpha-poly-oxymethylene, trioxane or other material that emits formaldehyde when heated.

4. The method of claim 1, wherein the desired gas is selected from the group consisting of 1,4-dichlorobenzene; 1,3,5-trichlorobenzene; 1,2,4,5-tetrachlorobenzene; 1,2,4,5-tetramethylbenzene; camphor; hexachlorobenzene; hexamethylcyclotrisiloxane; indole; menthol; naphthalene; p-cresol; phenol; or other low vapor pressure chemical.

5. The method of claim 4, wherein the parent compound is the solid, semi-solid or liquid form of the desired gas.

6. The method of claim 1, wherein the effusion tube has a temperature, and wherein the effusion tube is heated to a temperature no greater than 482 F.

7. The method of claim 1, wherein at least a portion of the heat to the effusion tube is provided by a means selected from the group consisting of heating tape, rope heater, heating cable, and heating cord in contact with the metal jacket.

8. The method of claim 1, wherein at least a portion of the heat to the effusion tube is provided by a tube furnace that heats the outside of the metal jacket.

9. The method of claim 1, wherein the desired gas is generated at a rate up to 50 grams per hour.

10. The method of claim 1, further comprising introducing a carrier gas, wherein the carrier gas blends with the desired gas and exits the open end of the metal jacket.

11. The method of claim 10, wherein the blended gas has a first flow rate, the carrier gas has a second flow rate, and the effusion tube has a first temperature, and wherein the first flow rate is controlled by adjusting the first temperature and/or the second gas flow rate.

12. The method of claim 10, wherein the carrier gas provides at least a portion of the heat to the effusion tube.

13. The method of claim 10, wherein the carrier gas is selected from the group consisting of nitrogen, helium, argon, air, and other gas that is non-reactive with the desired gas.

14. The method of claim 10, wherein the blended gas is produced at various pressures up to 2500 psig.

15. The method of claim 1, further comprising introducing the desired gas or the blended gas into a gas cylinder.

16. The method of claim 1, wherein once the desired gas is vaporized, the inert matrix retains the residue of the parent compound.

* * * * *